US011833449B2

(12) United States Patent
Akmal et al.

(10) Patent No.: US 11,833,449 B2
(45) Date of Patent: *Dec. 5, 2023

(54) METHOD AND DEVICE FOR SEPARATING AND MEASURING MULTIPHASE IMMISCIBLE FLUID MIXTURES

(71) Applicant: SAUDI ARABIAN OIL COMPANY, Dhahran (SA)

(72) Inventors: Naim Akmal, Dhahran (SA); Said Shahrani, Dhahran (SA); Saleh Sharidi, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 60 days.

This patent is subject to a terminal disclaimer.

(21) Appl. No.: 17/482,173

(22) Filed: Sep. 22, 2021

(65) Prior Publication Data

US 2023/0089975 A1 Mar. 23, 2023

(51) Int. Cl.
*B01D 17/02* (2006.01)
*B01D 17/06* (2006.01)
(Continued)

(52) U.S. Cl.
CPC ......... *B01D 17/0205* (2013.01); *B01D 17/06* (2013.01); *E21B 49/08* (2013.01); *G01N 27/10* (2013.01)

(58) Field of Classification Search
CPC ..... B01D 17/0205; B01D 17/05; E21B 49/08; G01N 27/10
See application file for complete search history.

(56) References Cited

U.S. PATENT DOCUMENTS 3,712,118 A * 1/1973 Mason ............... G01N 33/2823 73/61.59
4,481,130 A 11/1984 Robertson
(Continued)

FOREIGN PATENT DOCUMENTS

CN 101670197 B 12/2011
CN 102128658 B 7/2012
(Continued)

OTHER PUBLICATIONS

Andreussi et al. "Application of a wet gas meter to detect extremely low liquid volume fractions" BHR Group—Multiphase Production Technology 13 (Year: 2007).*
(Continued)

*Primary Examiner* — John Fitzgerald
(74) *Attorney, Agent, or Firm* — Bracewell LLP; Constance G. Rhebergen; Keith R. Derrington

(57) ABSTRACT

Methods and devices for obtaining approximate property data from the aqueous liquid phase of a multiphase fluid produced from a well. The method includes introducing a discrete sample of the multiphase fluid to a separation vessel; mixing a demulsifier with the discrete sample of the multiphase fluid; allowing the multiphase fluid to separate into separate liquid phases; drawing a measured sample of the aqueous liquid phase from the separation vessel, and diluting it with a measured amount of fresh water; analyzing the diluted aqueous liquid phase sample in a water analysis unit to measure a property of the diluted aqueous liquid phase sample and obtain diluted aqueous liquid phase sample data; and calculating the approximate aqueous liquid phase property data using the diluted aqueous liquid phase sample data and accounting for the amount of fresh water used to dilute the measured sample of the aqueous liquid phase.

9 Claims, 1 Drawing Sheet

100
120
101
108
106
121
104
110
105
130
131
107
111
141
190
180
140
150
160
170
144

(51) Int. Cl.

| | |
|---|---|
| ***E21B 49/08*** | (2006.01) |
| *G01N 27/10* | (2006.01) |

(56) References Cited

U.S. PATENT DOCUMENTS

| | | | | |
|---|---|---|---|---|
| 4,581,134 | A | 4/1986 | Richter, Jr. et al. | |
| 5,078,856 | A | 1/1992 | Yamaguchi et al. | |
| 5,637,201 | A | 6/1997 | Raguse et al. | |
| 5,741,409 | A | 4/1998 | Raguse et al. | |
| 5,753,093 | A | 5/1998 | Raguse et al. | |
| 6,004,442 | A | 12/1999 | Choulga et al. | |
| 6,872,239 | B2 | 3/2005 | Nilsen et al. | |
| 7,140,441 | B2 | 11/2006 | Hauge et al. | |
| 7,147,788 | B2 | 12/2006 | Tveiten | |
| 7,231,819 | B2 | 6/2007 | Jones et al. | |
| 7,373,813 | B2 | 5/2008 | DiFoggio | |
| 7,474,969 | B2 | 1/2009 | Poulisse | |
| 7,661,302 | B2 | 2/2010 | Gysling | |
| 7,775,085 | B2 | 8/2010 | Scott | |
| 7,966,892 | B1 * | 6/2011 | Halilah | G01N 33/2841 73/861.04 |
| 8,177,958 | B2 | 5/2012 | Lawrence et al. | |
| 8,720,573 | B2 | 5/2014 | Eriksen | |
| 8,790,509 | B2 | 7/2014 | Vu | |
| 8,935,100 | B2 | 1/2015 | Weiner et al. | |
| 9,052,285 | B2 | 6/2015 | Muller et al. | |
| 9,239,406 | B2 | 1/2016 | Kalia et al. | |
| 9,284,705 | B2 | 3/2016 | Theegala | |
| 9,314,715 | B2 | 4/2016 | Grave et al. | |
| 9,341,058 | B2 | 5/2016 | Keizer et al. | |
| 9,540,574 | B2 | 1/2017 | Janssen et al. | |
| 9,658,178 | B2 | 5/2017 | Surman et al. | |
| 9,696,193 | B2 | 7/2017 | Martin et al. | |
| 9,840,895 | B1 | 12/2017 | Kuhn | |
| 9,863,926 | B2 * | 1/2018 | Kriel | G01N 1/2211 |
| 10,023,811 | B2 | 7/2018 | Soliman et al. | |
| 10,260,010 | B2 | 4/2019 | Soliman | |
| 10,350,515 | B2 | 7/2019 | Al-Shafei et al. | |
| 10,597,313 | B2 | 3/2020 | Raynel et al. | |
| 2012/0111571 | A1 * | 5/2012 | Eriksen | G01F 1/74 166/336 |
| 2013/0026082 | A1 | 1/2013 | Al-Shafei et al. | |
| 2016/0052799 | A1 | 2/2016 | Grave et al. | |
| 2017/0319984 | A1 | 11/2017 | Oshinowo | |
| 2018/0244539 | A1 | 8/2018 | Asdahl et al. | |
| 2018/0299423 | A1 | 10/2018 | Leblanc | |
| 2019/0010796 | A1 | 1/2019 | De Freitas et al. | |
| 2019/0049425 | A1 | 2/2019 | Marshall et al. | |
| 2019/0211274 | A1 | 7/2019 | Soliman et al. | |
| 2020/0102234 | A1 | 4/2020 | Patton | |
| 2020/0255748 | A1 | 8/2020 | Soliman et al. | |
| 2021/0102831 | A1 | 4/2021 | Ahmad et al. | |
| 2022/0380688 | A1 * | 12/2022 | Soliman | B01D 17/12 |
| 2023/0086247 | A1 * | 3/2023 | Akmal | G01N 33/1886 204/263 |
| 2023/0089200 | A1 * | 3/2023 | Akmal | B01D 17/12 210/768 |
| 2023/0093403 | A1 * | 3/2023 | Akmal | G01N 1/10 73/61.44 |

FOREIGN PATENT DOCUMENTS

| | | | |
|---|---|---|---|
| WO | 2001074468 | A3 | 10/2001 |
| WO | 2021043923 | A1 | 3/2021 |

OTHER PUBLICATIONS

Rodriguez et al., "Treatment of Produced Water In the Permian Basin For Hydraulic Fracturing: Comparison of Different Coagulation Processes and Innovative Filter Media", MDPI Water, 12, 770, Mar. 11, 2020, pp. 1-16.

Ghorbani et al., "Validating Automated Real-Time Produced Water Composition Measurement Device With Field Produced Water Samples: A Pathway to Filed Trial", SPE-188244-MS, Nov. 13, 2017, 2 pages.

Hach, "Complete Water Analysis For The Upstream Oil & Gas Industry", 2014, 20 pages.

Hansen et al., "Multi-Phase Flow Metering In Offshore Oil and Gas Transportation Pipelines: Trends and Perspectives", WWW.mdpi.com/journal/sensors, 19, 2184, May 11, 2019, pp. 1-26.

Roach et al., "A Multiphase Flow Meter For the On-Line Determination of the Flow Rates of Oil, Water and Gas", AU9817323, 1997, CSIRO Minerals, pp. 106-111.

* cited by examiner

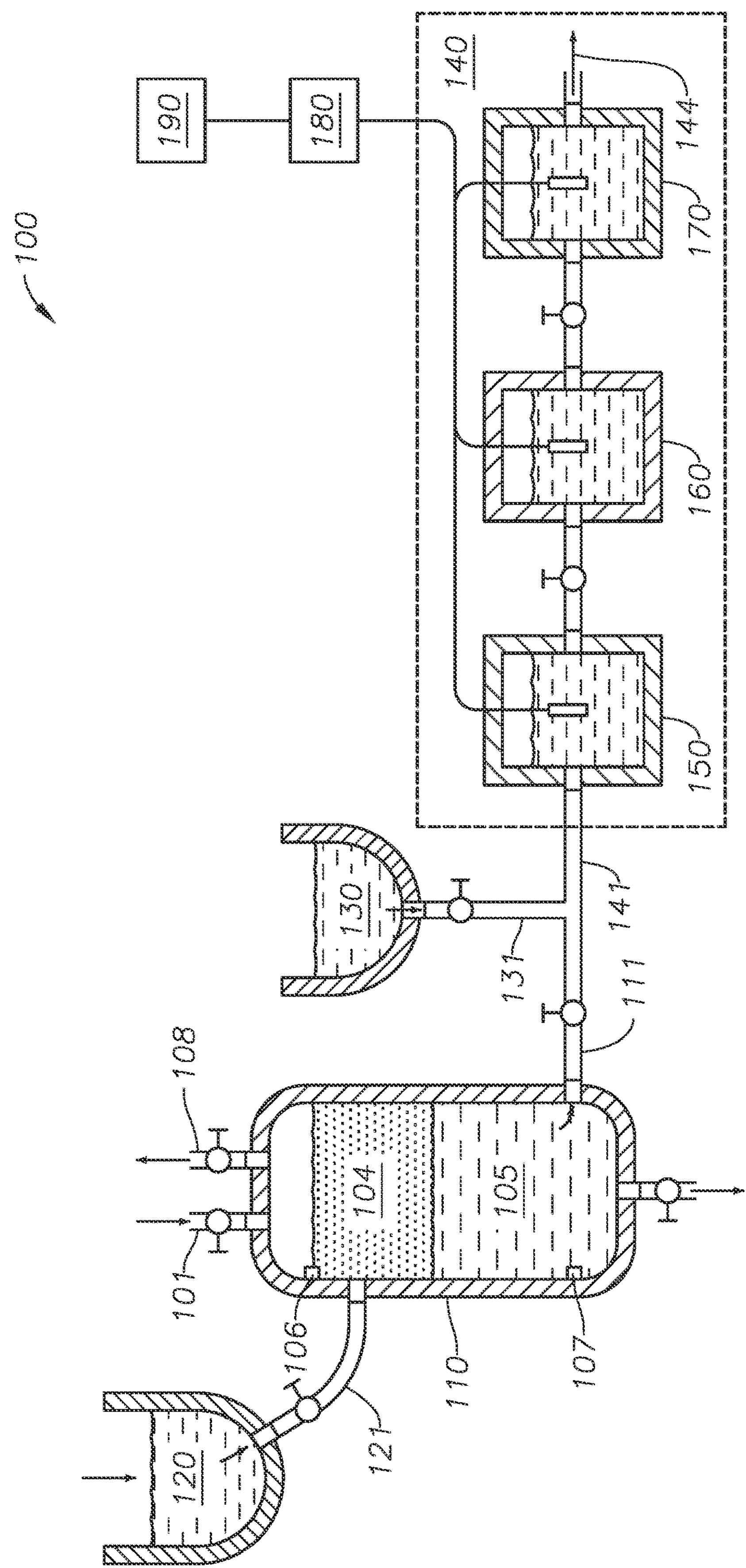
100
190
180
140
144
170
160
150
141
130
131
111
108
104
105
101
106
110
107
121
120

METHOD AND DEVICE FOR SEPARATING AND MEASURING MULTIPHASE IMMISCIBLE FLUID MIXTURES

BACKGROUND OF THE INVENTION

1. Technical Field

The disclosure relates to methods and apparatuses of separating and measuring multiphase fluid mixtures; particularly mixtures produced from hydrocarbon-bearing formations.

2. Discussion of Related Art

Fluids produced from hydrocarbon-bearing formations typically vary in their composition over time. Generally a greater amount of crude oil is produced initially. However, over time the amount of produced water increases and the amount of crude oil produced decreases. It is necessary to know the amount of crude oil and produced water produced from a given well in order to manage the well and oil field.

Conventionally, the amount of crude oil produced from a well is measured by analyzing samples of fluids produced from the well in a laboratory. Typically, a sample of a fluid is collected, the crude oil is allowed to separate from produced water in the sample, and a sample of the produced water is taken to a secondary filtration or separation unit where it is treated to remove any residual oil. A portion of the produced water is then analyzed in a laboratory to measure certain geophysical properties. The data obtained by this analysis is used to calibrate a multiphase flow meter.

SUMMARY OF THE INVENTION

Disclosed are processes and devices for separating and analyzing a multiphase fluid. The processes and devices allow for automated continuous analysis of discrete samples of a multiphase fluid, and can provide reliable and timely data for calibrating, optimizing, and controlling a multiphase flow meter.

Devices for separating and analyzing an aqueous liquid phase from a multiphase fluid produced from a hydrocarbon-bearing formation are disclosed. Such devices can include: a separation vessel; a demulsifier source in fluid communication with the separation vessel; a fresh water source; an aqueous liquid phase stream that can be configured to conduct the sample of the aqueous liquid phase from the separation vessel to be diluted with freshwater from the freshwater source; a water analysis unit; and a processing unit. The separation vessel can include an inner chamber for containing a discrete sample of the multiphase fluid; a multiphase fluid inlet to allow the discrete sample of the multiphase fluid to flow into the inner chamber of the separation vessel; and an aqueous liquid phase outlet in the separation vessel that can be configured for drawing a measured sample of an aqueous liquid phase from within the inner chamber. The demulsifier source can be configured to introduce a demulsifier to the inner chamber of the separation vessel. The freshwater source can be in fluid communication with the aqueous liquid phase stream and be configured such that a measured amount of fresh water can be introduced to the measured sample of the aqueous liquid phase to obtain a diluted aqueous liquid phase sample. The water analysis unit can be in fluid communication with the aqueous liquid phase stream and that can be configured to receive the diluted aqueous liquid phase sample and analyze the same, the water analysis unit having a sensor that can be configured to measure a property of the diluted aqueous liquid phase sample to obtain diluted aqueous liquid phase sample data. The processing unit can be configured to receive the diluted aqueous liquid phase sample data and calculate an approximate aqueous liquid phase data by accounting for the measured amount of fresh water used to dilute the measured sample of the aqueous liquid phase According to at least one embodiment, the water analysis unit comprises a sensor that can be configured to measure a property selected from the group consisting of total dissolved solids (TDS), salinity, pH, conductivity, sodium concentration, chloride concentration, sulfate concentration, carbonate concentration, nitrate concentration, and any combination of the same.

According to at least one embodiment, the sensor comprises an ion-selective electrode.

According to at least one embodiment, the separation vessel comprises a first level indicator, the first level indicator being configured to signal the stop of flow of the multiphase fluid through the multiphase fluid inlet when multiphase fluid rises to the level of the first level indicator.

According to at least one embodiment, the separation vessel comprises a second level indicator, the second level indicator being configured to signal an action upon emptying the multiphase fluid from the inner chamber of the separation vessel, the action can be an automated function selected from the group consisting of stopping the emptying of the multiphase fluid from the inner chamber of the separation vessel, flushing the inner chamber of the separation vessel with fresh water, introducing a subsequent discrete sample of the multiphase fluid to the inner chamber of the separation vessel, and any combination of the same.

According to at least one embodiment, the separation vessel comprises a gas vent configured to allow gas in the inner chamber of the separation vessel to vent as it is displaced by the discrete sample of the multiphase fluid being introduced to the inner chamber of the separation vessel.

According to at least one embodiment, the device can also include a flow meter configured to measure a flow of gas as it passes through the gas vent.

According to at least one embodiment, the device can also include a flow meter configured to measure flow of the measured sample of the aqueous liquid phase as it is drawn from the inner chamber of the separation vessel.

According to at least one embodiment, the device can also include a flow meter configured to measure flow of the measured amount of fresh water that is used to dilute the measured sample of the aqueous liquid phase to obtain the diluted aqueous liquid phase sample.

According to at least one embodiment, the processing unit can be configured to calculate the approximate aqueous liquid phase data by accounting for the measured amount of fresh water used to dilute the measured sample of the aqueous liquid phase and a corresponding property of the fresh water.

According to at least one embodiment, the separation vessel can be at least partially made of shatter-proof glass.

Methods of measuring an approximate aqueous liquid phase property data from a multiphase fluid that can be produced from a hydrocarbon-bearing formation and using the approximate aqueous liquid phase property data to calibrate a multiphase flow meter are also provided. Such methods can include the steps of: introducing a discrete sample of the multiphase fluid to a separation vessel; introducing and mixing a demulsifier with the discrete sample of the multiphase fluid in the separation vessel; allowing the multiphase fluid to separate in the separation vessel for a first period of time to obtain separate liquid phases including an aqueous liquid phase and a nonpolar liquid phase; drawing a measured sample of the aqueous liquid phase from the separation vessel, and diluting it with a measured amount of fresh water to obtain a diluted aqueous liquid phase sample; analyzing the diluted aqueous liquid phase sample in a water analysis unit to measure a property of the diluted aqueous liquid phase sample and obtain diluted aqueous liquid phase sample data; calculating the approximate aqueous liquid phase property data by adjusting the diluted aqueous liquid phase sample data to account for the measured amount of fresh water used to dilute the measured sample of the aqueous liquid phase; and using the approximate aqueous liquid phase property to calibrate the multiphase flow meter.

According to at least one embodiment, the property of the diluted aqueous liquid phase sample can be selected from the group consisting of total dissolved solids (TDS), salinity, pH, conductivity, sodium concentration, chloride concentration, sulfate concentration, carbonate concentration, nitrate concentration, and any combination of the same.

According to at least one embodiment, the step of analyzing the diluted aqueous liquid phase sample in a water analysis unit can be carried out using a sensor having an ion-selective electrode.

According to at least one embodiment, direct physical contact between the diluted aqueous liquid phase sample and the sensor can be maintained for a second period of time that can be between 30 seconds and 1 hour.

According to at least one embodiment, the first period of time can be between 20 minutes and 24 hours.

According to at least one embodiment, the method can include flushing the water analysis unit with fresh water after analyzing the diluted aqueous liquid phase sample.

According to at least one embodiment, the method can include emptying the inner chamber of the separation vessel and flushing and flushing it with fresh water.

According to at least one embodiment, the water analysis unit and the inner chamber of the separation vessel can be emptied and the steps can be repeated continuously.

According to at least one embodiment, the steps can be carried out over a third period of time that can be between 5 minutes and 6 hours.

BRIEF DESCRIPTION OF THE DRAWING

The embodiments disclosed will be understood by the following detailed description along with the accompanying drawing. The embodiments shown in the FIGURE only illustrate several embodiments of the disclosure. The disclosure admits of other embodiments not shown in the FIGURE, and is not limited to the content of the illustrations. Similar streams, units, or features may have similar reference labels in the drawings.

FIG. 1 is a schematic illustration of a process and device for separating and analyzing an aqueous liquid phase sample from a discrete sample of a multiphase fluid mixture.

DETAILED DESCRIPTION OF THE DRAWING

For certain embodiments, many details are provided for thorough understanding of the various components or steps. In other instances, known processes, devices, compositions, and systems are not described in particular detail so that the embodiments are not obscured by detail. Likewise, illustrations of the various embodiments can omit certain features or details so that the various embodiments are not obscured. In the FIGURES, fluid streams can be represented by lines. A person of ordinary skill will understand that fluid streams can be conveyed by various means, including but not limited to pipes, conduit, channels, and their attachments and fittings. Though other equipment, such as pumps, valves, storage tanks, reflux drums, reflux streams, controllers, switches, valves, and so forth, may be present in various embodiments, such equipment is not shown in the figures for the sake of clarity.

The description can use the phrases “in some embodiments,” “in various embodiments,” “in an embodiment,” “in at least one embodiment,” or “in embodiments,” which can each refer to one or more of the same or different embodiments. Furthermore, the terms “comprising,” “including,” “having,” and the like, as used with respect to embodiments of the present disclosure are synonymous.

In this disclosure and the appended claims, unless otherwise indicated, all numbers expressing quantities, percentages or proportions, and other numerical values used in the specification and claims are to be understood as being modified in all instances by the term “about.” The term “about” applies to all numeric values, whether or not explicitly indicated.

Ranges can be expressed in this disclosure as from about one particular value and to about another particular value. With these ranges, another embodiment is from the one particular value to the other particular value, along with all combinations within the range. When the range of values is described or referenced in this disclosure, the interval encompasses each intervening value between the upper limit and the lower limit, as well as the upper limit and the lower limit; and includes lesser ranges of the interval subject to any specific exclusion provided.

Ordinal numbers (such as “first,” “second,” “third,” and so on), when used in this disclosure as an adjectives before a term, merely identify a particular component, feature, step, or combination of these unless expressly provided otherwise. At times, ordinal numbers may be used to distinguish a particular feature, component, or step from another feature, component, or step that is described by the same term or similar term. Unless expressly provided otherwise, ordinal numbers do not indicate any relationship, order, quality, ranking, importance, or characteristic between features, components, steps, or combinations of these. Moreover, ordinal numbers do not define a numerical limit to the features, components, steps, or combination they identify.

Where a method comprising two or more defined steps is recited or referenced in this disclosure, or the appended claims, the defined steps can be carried out in any order or simultaneously except where the context excludes that possibility.

Having an accurate view of the hydrocarbons produced from one or more wells enables operators to make decisions regarding the economic potential of one or more wells, and the oil field more generally. Advantageously, the methods and apparatuses disclosed here are capable of providing near-instantaneous fluid measurements to support such decisions. Wells producing a significant water cut can be identified, and isolated if necessary, so that resources are conserved. Because the processes and devices can be automated, measurements can be carried out routinely with minimal labor costs and reduced potential for error. Moreover, the design of the methods and devices enables the use of materials that would otherwise be unsuitable because of corrosion. In an aspect, the processes and devices allow for the use of sensors which would otherwise be unsuitable. The data obtained using the processes and devices disclosed can be used to calibrate, optimize, or control a multiphase flow meter, for example, at a gas-oil separation plant. The data may also be used to assess the remaining productivity of a producing well.

FIG. 1 is a schematic illustration of a process and device for separating and measuring a multiphase fluid. In FIG. 1, the system 100 includes a separation vessel 110 having an inner chamber. The separation vessel 110 has a first level indicator 106 and a second level indicator 107. The first level indicator 106 and second level indicator 107 can be used to control the flow of the multiphase fluid into and out of the separation vessel. For example, the first level indicator 106 can be configured to trigger flow of the multiphase fluid to stop when the inner chamber of the separation vessel 110 is full, and the second level indicator 107 can be configured to trigger filling of the inner chamber of the separation vessel 110 with a discrete sample of the multiphase fluid after it has been emptied. The first level indicator 106 and second level indicator 107 can be any device suitable for indicating the level of liquid held in the inner chamber of the separation vessel 110, such as a sensor, a window, a float, etc. Though FIG. 1 shows two level indicators (i.e., first level indicator 106 and second level indicator 107), a person of ordinary skill will appreciate that some embodiments can use a single level indicator, and others may use more than two level indicators. For example, a window can be provided in the separation vessel 110 that extends in a vertical direction from top to bottom such that the liquid level can be observed at various points. In another example, a sensor can be provided at or near the top of the inner chamber to measure the distance between the sensor and the surface of the liquid contained in the separation vessel. In at least one embodiment, a separation vessel can be manufactured from an at least partially translucent or transparent material such that the level of liquid inside the vessel can be determined by observation from outside the separation vessel. In at least one embodiment, the separation vessel can be made of shatter-proof glass and can include markings for measuring the volume of liquid contained within. In at least one embodiment, the level indicator can be omitted.

A discrete sample of a multiphase fluid is delivered to separation vessel 110 by multiphase fluid stream 101. The multiphase fluid can be characterized as a fluid that includes a mixture of at least an aqueous liquid phase and a nonpolar liquid phase. Analyzing discrete samples allows greater control over the separation of aqueous liquid and nonpolar liquid phases than could be achieved using a continuous process. In some embodiments, the multiphase fluid can include aqueous liquid droplets dispersed in the nonpolar liquid phase, nonpolar liquid droplets dispersed in the aqueous liquid phase, or both. The multiphase fluid can include an emulsion of aqueous liquid droplets emulsified in the nonpolar liquid phase, nonpolar liquid phase droplets emulsified in the aqueous liquid phase, or both. The aqueous liquid phase can include produced water from a hydrocarbon-bearing formation. The nonpolar liquid phase can include crude oil produced from a hydrocarbon-bearing formation. The multiphase fluid can contain between about 5 and 95 vol % nonpolar liquid phase and between about 5 and 95 vol % aqueous liquid phase. If the multiphase fluid contains less than about 5 vol % aqueous liquid phase there may not be a sufficient amount of water in the discrete sample to carry out analysis of its geophysical properties. According to at least one embodiment, the multiphase fluid can have a volume ratio of nonpolar liquid phase to aqueous liquid phase that is between about 99:1 and 30:70, alternately between about 95:5 and 40:60. In one or more embodiments, the multiphase fluid includes a gas phase. The gas phase can include gases produced from a hydrocarbon-bearing formation, such as hydrocarbons, carbon oxides, hydrogen sulfide, mercaptans, etc. The gas phase can be dissolved in the liquid phases of the multiphase fluid when it is introduced to the separation vessel 110.

In at least one embodiment, the multiphase fluid can be a fluid extracted from a hydrocarbon-bearing formation. In at least one embodiment, the multiphase fluid can be processed to remove dissolved gases. In some embodiments, the multiphase fluid can be collected in a test trap (e.g., a high pressure production trap or low pressure production trap), and then flown to the separation vessel 110. In at least one embodiment, the multiphase fluid can be provided from a high-pressure sample line.

As the inner chamber of the separation vessel 110 is filled with the multiphase fluid, gases displaced by the multiphase fluid exit the separation vessel 110 in gas vent stream 108. The gas vent stream 108 can also be used to vent gases that come out of solution during or after filling the separation vessel 110. The gas that is vented from the separation vessel 110 through gas vent stream 108 can be measured using a flow meter (not shown).

A measured amount of demulsifier from a demulsifier source 120 is introduced to the separation vessel 110 by demulsifier stream 121 and is mixed with the multiphase fluid to obtain a demulsified multiphase fluid. The demulsifier source 120 can be any container or vessel (e.g., reservoir, tank, tube, injector, etc.) suitable for storing the demulsifier. In some embodiments, the demulsifier can be mixed with the multiphase fluid before being introduced to the separation vessel 110. In some embodiments, the demulsifier can be actively mixed with the multiphase fluid using a mixer (not shown). The demulsifier can be any component, such as a surface-active agent, that facilitates the aggregation of dispersed droplets of the aqueous liquid phase or the nonpolar liquid phase. The type of demulsifier can be selected based on the type of crude oil and the amount of produced water that is typically produced. Nonlimiting examples of suitable demulsifiers include: polyol block copolymers, alkoxylated alkyl phenol formaldehyde resins, epoxy resin alkoxylates, amine-initiated polyol block copolymers, modified silicone polyethers, silicone polyethers, or similar components, and combinations of the same. Such demulsifiers are available from The Dow Chemical Company, Inc. and Ecolab, Inc. The amount of demulsifier that is used can be an amount sufficient to facilitate the aggregation of dispersed droplets of the aqueous liquid phase or nonpolar liquid phase such that the bulk aqueous liquid phase and nonpolar liquid phase are separated. However, excess demulsifier can slow separation of the multiphase fluid and produce very stable emulsions. According to at least one embodiment, the amount of demulsifier can be enough to produce a concentration of between about 1 and 100 ppmv demulsifier, alternately between about 1 and 50 ppmv, alternately between about 1 and 25 ppmv, alternately between about 5 and 10 ppmv. In FIG. 1, the multiphase fluid has been mixed with the demulsifier to obtain a separated nonpolar liquid phase 104 and a separated aqueous liquid phase 105. The multiphase fluid is allowed to separate for a period of time. In at least one embodiment, the period of time can be between about 1 minute and 24 hours, preferably between about 20 minutes and 12 hours, more preferably between about 1 and 5 hours. According to at least one embodiment, the period of time can be about 2 hours.

After separating the aqueous liquid phase and the nonpolar liquid phase, at least a portion of the aqueous liquid phase is drawn from the separation vessel 110 and conducted by aqueous liquid phase stream 111. The separation vessel 110 can have an aqueous liquid phase outlet that is configured to draw the sample of the aqueous liquid phase. For example, the aqueous liquid phase outlet can be located in a portion of the separation vessel 110 where the aqueous liquid phase outlet is likely to accumulate. In many cases, the aqueous liquid phase will be denser than the nonpolar liquid phase and well settle beneath the nonpolar liquid phase. Therefore, the aqueous liquid phase outlet can be located in a lower portion of the separation vessel 110. In at least one embodiment, the aqueous liquid phase outlet can be the opening of a tube, pipe, or conduit that is located in a portion of the separation vessel 110 where the aqueous liquid phase is likely to accumulate after separating. The aqueous liquid phase sample can be drawn by any means suitable for drawing a liquid such as siphoning, pouring, pumping, etc.

Fresh water from fresh water reservoir 130 is delivered by freshwater stream 131 to aqueous liquid phase stream 111 and is mixed with the aqueous liquid phase sample to obtain a diluted aqueous liquid phase sample. The amount (i.e., mass, volume, or both) of the aqueous liquid phase that is mixed with the fresh water can be measured using known methods and instruments, and the measurement can be sent to processing unit 180. Likewise, the amount (i.e., volume, mass, or both) of fresh water that is used to dilute the aqueous liquid phase sample can be measured using known methods and instruments, and the measurement sent to processing unit 180. The amount of fresh water used to dilute the aqueous liquid phase sample can be predetermined based on conditions, characterization of produced water, application requirements, or a combination of the same. In at least one embodiment, the amount of aqueous liquid phase sample and the amount of fresh water used to dilute the aqueous liquid phase sample can be predetermined. In at least one embodiment, the fresh water can be deionized water. In at least one embodiment, the ratio of fresh water to aqueous liquid phase sample in the diluted aqueous liquid phase sample can be between about 50:1 and 1:1, preferably between about 30:1 and 1:1, more preferably between about 5:1 and 20:1. The diluted aqueous liquid phase sample is conducted by diluted aqueous liquid phase sample stream 141 to water analysis unit 140.

Water analysis unit 140 includes one or more sensors for measuring one or more physical or chemical properties of the diluted aqueous liquid phase sample. In at least one embodiment, the water analysis unit 140 includes one or more sensors for measuring properties of the diluted aqueous liquid phase sample including total dissolved solids (TDS), salinity, pH conductivity, sodium concentration, chloride concentration, sulfate concentration, carbonate concentration, nitrate concentration, etc., or any combination of the same. An example of a suitable sensor for measuring one or more physical or chemical properties can be an ion-selective electrode, such as those available commercially and known to one of ordinary skill. Preferably, the sensor can be an ion-selective electrode having a stainless steel body and a sensing area that is covered with a layer of an ion-exchange polymer to protect the sensor from corrosion. Diluting the aqueous liquid phase sample with fresh water ensures that the capacity of the sensors is not overloaded and increases the volume of relatively small samples so that they can be analyzed. This step can also reduce the corrosive potential of the aqueous liquid sample, allowing system components to be manufactured from materials which would otherwise be unsuitable.

In FIG. 1, water analysis unit 140 includes three flow cells: first flow cell 150, second flow cell 160, and third flow cell 170. Each flow cell can include a sensor for measuring a property of the diluted aqueous liquid phase sample. Though the flow cells in FIG. 1 are shown in series, it should be appreciated that in some embodiments the flow cells can also be configured in parallel. In at least one embodiment, multiple sensors can be used in a single flow cell. In at least one embodiment, the diluted aqueous liquid phase sample is allowed to remain in contact with the one or more sensors for a period of time such that a stable reading is obtained. In at least one embodiment, the period of time can be between 30 seconds and 1 hour, preferably between about 1 minute and about 20 minutes, more preferably between about 5 minutes and 15 minutes. Diluted aqueous liquid phase sample data from the one or more sensors is sent to a processing unit 180 where it is recorded. The processing unit 180 can be configured to calculate approximate corresponding values from the diluted aqueous liquid phase sample data for the nondiluted aqueous liquid phase sample by adjusting the diluted aqueous liquid phase sample data to account for the amount of dilution. For example, if the property of the aqueous liquid phase can be approximated using a linear equation, an approximate aqueous liquid phase property data value for the nondiluted aqueous liquid phase sample can be calculated using Eqn. 1.

$$Y = X_1 + \frac{V_f}{V_i}(X_1 - X_0) \qquad \text{Eqn. 1}$$

Where $X_0$ is the value of the observed property of the fresh water, $X_1$ is the value of the observed property of the diluted aqueous liquid phase sample, $V_f$ is the volume of fresh water, $V_i$ is the volume of the portion of the aqueous liquid phase that is drawn from the separation vessel 110 before it is diluted, and Y represents the approximate value of the corresponding property for the nondiluted aqueous liquid phase sample. The processing unit 180 can also be configured to adjust the calculated data to account for the properties of the fresh water. For example, if the property to be approximated is the concentration of a solute, the processing unit 180 can be configured to adjust the calculated data to account for a known preexisting concentration of the solute in the fresh water that is used to dilute the aqueous liquid phase sample. In at least one embodiment, the processing unit 180 can be a distributed control system.

The approximate value or values calculated by the processing unit 180 can be used to calibrate, optimize, or control a multiphase flow meter 190. In at least one embodiment, the multiphase flow meter 190 is used to measure the flow of oil and produced water at a gas-oil separation plant. In at least one embodiment, the multiphase flow meter 190 is used to measure the flow of oil and produced water at a well. The system 100 can be used to analyze discrete multiphase fluid samples from individual wells, allowing less-productive wells to be identified. In at least one embodiment, the period of time measured from the introduction of the discrete sample of the multiphase fluid to the inner chamber of the separation vessel 110 to the calibration of the multiphase flow meter 190 can be between about 5 minutes and 24 hours, alternatively between about 5 minutes and 10 hours, preferably between 5 minutes and 6 hours, more preferably between about 30 minutes and 3 hours.

After the diluted aqueous liquid phase sample has been analyzed, it is removed from the water analysis unit 140 in water analysis effluent 144. Fresh water from fresh water reservoir 130 can be used to flush the water analysis unit 140 and prepare it to receive subsequent samples. The inner chamber of the separation vessel 110 is emptied through separation vessel effluent 113. In at least one embodiment, the inner chamber of the separation vessel 110 can be flushed with fresh water in preparation for receiving the next sample. The process can then be repeated with a new discrete sample of the multiphase fluid. The process can be automated so that discrete samples of the multiphase fluid are continuously measured, recorded, and used to calibrate, optimize, or control the multiphase flow meter 190 with minimal or no supervision. Automation of the process allows direct feeding of data to streamline and expedite the process of well monitoring while reducing error.

EXAMPLES

The following examples are included to demonstrate embodiments of the disclosure, and should be considered nonlimiting. The examples which follow represent techniques, systems, compositions, and apparatuses discovered to function well in the practice of the disclosure, and thus can be considered to constitute modes for its practice. However, changes can be made to the embodiments disclosed in the examples without departing from the spirit and scope of the disclosure.

Example 1—Laboratory-Scale Experiment Using a System for Separating a Multiphase Fluid, and Diluting and Analyzing the Aqueous Liquid Phase A laboratory-scale experiment was carried out using a system for separating a multiphase fluid, and diluting and analyzing the aqueous liquid phase. The multiphase fluid that was used was taken from a gas-oil separation plant. The system included a separation vessel made of shatter-proof glass, and having a configuration similar to the system shown in FIG. 1. The system was configured to fill the separation vessel with a multiphase fluid including crude oil, introduce a demulsifier, and allow separation of the aqueous liquid phase and the nonpolar liquid phase to be carried out for a period of about 2 hours. The aqueous liquid phase and the nonpolar liquid phase separated after about 2 hours and 15 minutes, with the aqueous liquid phase settling underneath the nonpolar liquid phase.

A measured amount of the aqueous liquid phase was automatically drawn from the lower portion of the inner chamber of the separation vessel, diluted with a measured amount of fresh water including deionized water from a fresh water reservoir, and sent to a water analysis unit. The water analysis unit included three flow cells in series, each having a sensor: a TDS sensor, chloride sensor, and salinity sensor respectively. The diluted sample was allowed to settle in each flow cell for 10 minutes, so that readings from the sensors were stable. Data from the sensors was sent to a data collection panel. The water analysis unit was configured to carry out the analysis automatically. The observed data was adjusted for the amount of dilution, and recorded.

After the diluted aqueous liquid phase sample was analyzed in the water analysis unit, the flow cells in the water analysis unit and the inner chamber of the separation vessel were flushed with deionized water, and the process was repeated with a subsequent discrete multiphase fluid sample. The measured and calculated values were compared with values obtained using conventional laboratory techniques, and the difference for each property was within plus or minus 5%. The sample preparation, analysis, and calculation of the values The drawings provide an illustration of certain embodiments. Other embodiments can be used, and logical changes can be made without departing from the scope of this disclosure. This disclosure is intended to disclose certain embodiments with the understanding that many other undisclosed changes and modifications can fall within the spirit and scope of the disclosure. The patentable scope is defined by the claims, and can include other examples that occur to those skilled in the art. Such other examples are intended to be within the scope of the claims if they have structural elements that do not differ from the literal language of the claims, or if they include equivalent structural elements with insubstantial differences from the literal language of the claims.

Unless otherwise defined, all technical and scientific terms used in this specification and the appended claims have the same meanings as commonly understood by one of ordinary skill in the relevant art.

We claim:

1. A method of measuring an approximate aqueous liquid phase property data from a multiphase fluid that is produced from a hydrocarbon-bearing formation and using the approximate aqueous liquid phase property data to calibrate a multiphase flow meter, the method comprising the steps of:

introducing a discrete sample of the multiphase fluid to a separation vessel;

introducing and mixing a demulsifier with the discrete sample of the multiphase fluid in the separation vessel;

allowing the multiphase fluid to separate in the separation vessel for a first period of time to obtain separate liquid phases comprising an aqueous liquid phase and a nonpolar liquid phase;

drawing a measured sample of the aqueous liquid phase from the separation vessel, and diluting it with a measured amount of fresh water to obtain a diluted aqueous liquid phase sample;

analyzing the diluted aqueous liquid phase sample in a water analysis unit to measure a property of the diluted aqueous liquid phase sample and obtain diluted aqueous liquid phase sample data;

calculating the approximate aqueous liquid phase property data by adjusting the diluted aqueous liquid phase sample data to account for the measured amount of fresh water used to dilute the measured sample of the aqueous liquid phase;

using the approximate aqueous liquid phase property to calibrate the multiphase flow meter.

2. The method of claim 1, in which the property of the diluted aqueous liquid phase sample is selected from the group consisting of total dissolved solids (TDS), salinity, pH, conductivity, sodium concentration, chloride concentration, sulfate concentration, carbonate concentration, nitrate concentration, and any combination of the same.

3. The method of claim 1, in which the first period of time is between 20 minutes and 24 hours.

4. The method of claim 1, further comprising flushing the water analysis unit with fresh water after analyzing the diluted aqueous liquid phase sample.

5. The method of claim 1, in which the steps are carried out over a third period of time that is between 5 minutes and 6 hours.

6. The method of claim 1, in which the step of analyzing the diluted aqueous liquid phase sample in a water analysis unit is carried out using a sensor comprising an ion-selective electrode.

7. The method of claim 6, in which direct physical contact between the diluted aqueous liquid phase sample and the sensor is maintained for a second period of time that is between 30 seconds and 1 hour.

8. The method of claim 1, further comprising emptying the inner chamber of the separation vessel and flushing and flushing it with fresh water.

9. The method of claim 8, in which the water analysis unit and the inner chamber of the separation vessel are emptied and the steps are repeated continuously.

* * * * *